United States Patent [19]

Maryanoff

[11] Patent Number: 5,399,757
[45] Date of Patent: Mar. 21, 1995

[54] PROCESS FOR THE PREPARATION OF N-(4-HYDROXYPHENYL)-RETINAMIDE

[75] Inventor: Cynthia A. Maryanoff, New Hope, Pa.

[73] Assignee: Ortho Pharmaceutical Corporation, Raritan, N.J.

[21] Appl. No.: 95,075

[22] Filed: Jul. 20, 1993

[51] Int. Cl.⁶ ............................................ C07C 231/02
[52] U.S. Cl. ............................ 564/133; 556/410; 564/182; 564/184
[58] Field of Search ............... 564/133, 184, 182; 556/410

[56] References Cited

U.S. PATENT DOCUMENTS 4,468,395  8/1984  Vorbrügen et al. ................ 424/246
4,743,400  5/1988  Maryanoff .......................... 564/188

OTHER PUBLICATIONS

Burgert et al., Chem. Ber. 120, 691–694, 1987.

Primary Examiner—Shailendra Kumar

[57] ABSTRACT

This invention is directed to an efficient, mild, high yield process for the large scale synthesis of N-(4-hydroxyphenyl)-retinamide comprising the preferred steps of reacting retinoic acid with dimethylchloroformamidinium chloride to from retinoyl chloride which in turn is reacted with bis-(N,O)-trimethylsilyl-p-aminophenol to eventually form N-(4-hydroxyphenyl)-retinamide and to the novel use of bis-(N,O)-trimethylsilyl-p-aminophenol to eventually form a hydroxyphenylamide, particularly N-(4-hydroxyphenylretinamide and methods of recrystallizing N-(4-hydroxyphenyl)-retinamide to obtain the stable "A" polymorph thereof.

20 Claims, No Drawings

PROCESS FOR THE PREPARATION OF N-(4-HYDROXYPHENYL)-RETINAMIDE

FIELD OF THE INVENTION

This invention is directed to a mild, high yield process for the large scale synthesis of N-(4-hydroxyphenyl)-retinamide. More particularly, in preferred embodiments, the process comprises the steps of reacting retinoic acid with dimethylchloroformamidinium chloride to form retinoyl chloride which in turn is reacted with bis-(N,O)-trimethylsilyl-p-aminophenol to form N-(4-hydroxyphenyl)-retinamide.

BACKGROUND OF THE INVENTION

N-(4-hydroxyphenyl)-all-trans-retinamide, also known as 4-HPR or fenretinide and having CAS registry number 65646-68-6, is described in U.S. Pat. Nos. 4,190,594 and 4,323,581 and has the following formula:

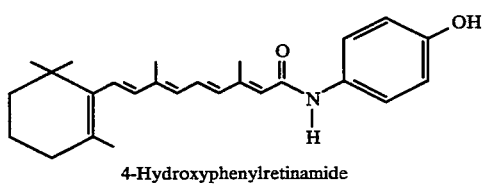

4-Hydroxyphenylretinamide

4-HPR protects against mammary cancer in rats induced with N-nitroso-N-methyl urea, and is less toxic when given orally to rats then retinoyl acetate and retinoic acid, See R. C. Moon et al., *Cancer Research*, Vol. 39, 1979, 1339-13464.

Prior art processes (Scheme 1) for preparing 4-HPR, use agents such as thionyl chloride or phosphorus trichloride for acyl chloride formation.

Common problems associated with using the above-described agents include the instability of retinoic acid and retinoyl chloride in their presence and their use disadvantageously results in the formation of a polymeric by-product which must be removed from the retinoyl chloride before conversion to 4-HPR. Additionally the formation of 4-HPR from retinoyl chloride with p-aminophenol requires heating. The use of the thionyl chloride method is also not amenable to scale-up because of the dilute concentrations of retinoid ($\leq 0.2M$) necessary to obtain reasonable yields and the precipitated pyridine hydrochloride causes handling problems on a large scale. Further, generation of retinoyl chloride using phosphorus trichloride requires temperatures of at least 50° C. to go to completion rapidly. Since solutions of retinoyl chloride are prone to light, heat, oxygen and base-catalyzed decomposition, these methods are simply not practical for scale up. Although these processes give acceptable yields (70-80%) on a small scale (0.1M), very low yields (20-25%) are obtained on scales greater than 1M. These low yields are due to the sensitivity of the retinoyl chloride intermediate and 4-HPR to light, heat, oxygen and base-catalyzed decomposition. See e.g. M. B. Sporn, A. B. Roberts, D. S. Goodman (eds.) *The Retinoids*, Vol. 1, 1984, Academic Press Inc., Orlando and A. R. Oyler, M. G. Motto, R. E. Naldi, K. L. Facchine, P. F. Hamburg, D. J. Burinsky, R. Dunphy, and M. L. Cotter, *Tetrahedron*, Vol. 45, 1989, 7679.

Since retinoic acid starting material is relatively costly, the intermediates and the final product (4-HPR) are sensitive, and the yields of available preparations are low for greater than small scale preparations, the efficiency advantages of a mild, high yield synthesis suitable for large scale (>1M) production are apparent.

An alternative process for preparing retinoyl chlorides is disclosed in U.S. Pat. No. 4,743,400 to Maryanoff which issued May 10, 1988 (U.S. Pat. No. 4,743,400) which avoids the use of prior art chlorinating agents such as thionyl chloride or phosphorus trichloride and the problems described at column 1, lines 21 to column 2, line 9 therein. U.S. Pat. No. 4,743,400 discloses process for producing retinoyl chloride using a dimethylchloroformamidinium chloride as the chlorinating agent. The entire disclosure of U.S. Pat. No. 4,743,400 is hereby incorporated herein by reference.

The process of U.S. Pat. No. 4,743,400 avoids some of the problems associated with thionyl chloride and phosphorus trichloride for producing the reagent retinoyl chloride.

The use of retinoyl chloride to produce 4-HPR by conventional reaction with p-aminophenol, however, provides unacceptably low product yields at larger scales for the reasons described above, i.e. sensitivity of the retinoyl chloride reaction intermediate and the

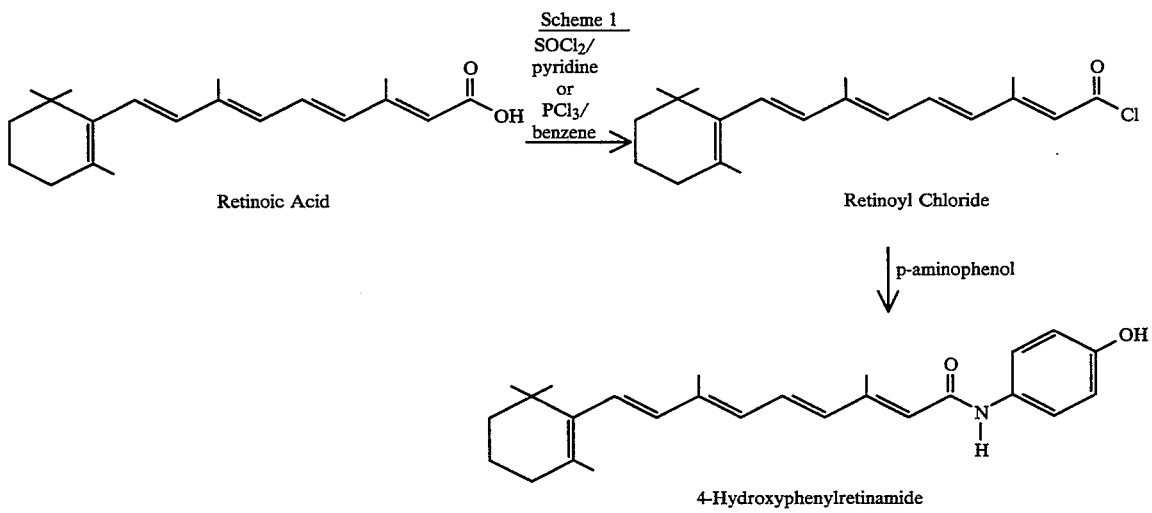

Scheme 1 product 4-HPR to light, heat, oxygen and base-catalyzed decomposition.

It is therefore, an object of the present invention to provide a process for the preparation of 4-HPR which is amenable to large scale production at high yields. It is a further and interrelated object of this invention to develop mild conditions for the preparation of 4-HPR to minimize decomposition and provide an efficient and high yielding large scale synthesis of high purity 4-HPR.

SUMMARY OF THE INVENTION

As embodied and fully described herein, the present invention provides an efficient, mild and high yield process for the large scale synthesis of N-(4-hydroxyphenyl)-retinamide (4-HPR) comprising the steps of reacting retinoic acid with dimethylchloroformamidinium chloride at ambient temperature to form retinoyl chloride; and reacting retinoyl chloride with a tertiary substituted bis-(N,O)-(silyl)-p-aminophenol of the formula bis-($R_1,R_2$, $R_3$silyl)-p-aminophenol wherein $R_{1-3}$ are the same or different and are phenyl or $C_{1-5}$ alkyl, more preferably bis-(N,O)-trimethylsilyl-p-aminophenol is utilized; the reaction is conducted at a temperature of under 20° C., preferably between 0°–20° C., and more preferably between 5°–12° C. to form 4-HPR.

In preferred embodiments the retinoic acid, retinoyl chloride and 4-HPR are the substantially pure trans-sterioisomer thereof. In accordance with preferred embodiments the yield of 4-HPR is at least 80% from retinoic acid.

In preferred embodiments of the invention retinoic acid is reacted preferably in a polar or dipolar aprotic solvent, more preferably in a solvent selected from the group consisting of N,N-dimethylformamide (DMF); N,N-dimethylacetamide; and N-methylpyrrolidinone. Most preferably, retinoic acid is reacted in a dimethylformamide solvent in the absence of a decomposition-catalyzing base, e.g. pyridine.

In other preferred embodiments of the invention retinoyl chloride is reacted with bis-(N,O)-trimethylsilyl-p-aminophenol in a polar or dipolar aprotic solvent, more preferably in a solvent selected from the group consisting of N,N-dimethylformamide (DMF); N,N-dimethylacetamide; and N-methylpyrrolidinone. Most preferably, retinoyl chloride is reacted with bis-(N,O)-trimethylsilyl-p-aminophenol in a dimethylformamide solvent.

In other particularly preferred embodiments of the invention the bis-(N,O)-trimethylsilyl-p-aminophenol is prepared by reacting p-aminophenol and hexamethyldisilazane.

In other preferred embodiments of the invention the 4-HPR is eventually formed and isolated by the additional steps of: adding an aqueous solution of potassium fluoride to the reaction mixture of dimethylformamide and 4-HPR to form a crystalline solvate thereof; and subsequently recrystallizing the solvate in an ethanol/water or toluene/acetone solution to provide substantially pure 4-HPR. Preferably, the ratio of ethanol/water is from about 2 to 10:1 at a concentration of 4-HPR of from about 10 to 20% weight by total weight of the solution. In preferred embodiments the crystallization temperature is from about 0° to 80° C.

As embodied and broadly described herein the invention provides a novel method of using bis-($R_1,R_2$, $R_3$silyl)-p-aminophenol, wherein $R_{1-3}$ are as described above, as an intermediate for producing hydroxyphenylamides, preferably using the compound bis-(N,O)-trimethylsilyl-p-aminophenol as an intermediate for preparing 4-HPR.

As embodied and broadly described herein the invention provides a novel method of forming the "A" polymorph of crystalline N-(4-hydroxyphenyl)-retinamide comprising the step of recrystallizing crude N-(4-hydroxyphenyl)-retinamide from a 10 to 20% weight by total weight concentration solution in an ethanol/water solvent having a ratio of from about 2 to 10:1 of ethanol:water and at a crystallization temperature of about 0° to 80° C.

DETAILED DESCRIPTION OF PREFERRED EMBODIMENTS OF THE INVENTION

Reference will now be made in detail to particularly preferred embodiments of the invention. Examples of the preferred embodiments are illustrated in the following Examples section.

As described above, solutions of retinoic acid, retinoyl chloride and 4-HPR are prone to rapid light, oxygen, heat and base-catalyzed decomposition. The emphasis of the process of the invention (Scheme 2 below) is to efficiently form retinoyl chloride in a short reaction time in high yield and purity and then react it in situ with an activated substrate to give 4-HPR rapidly in high yield.

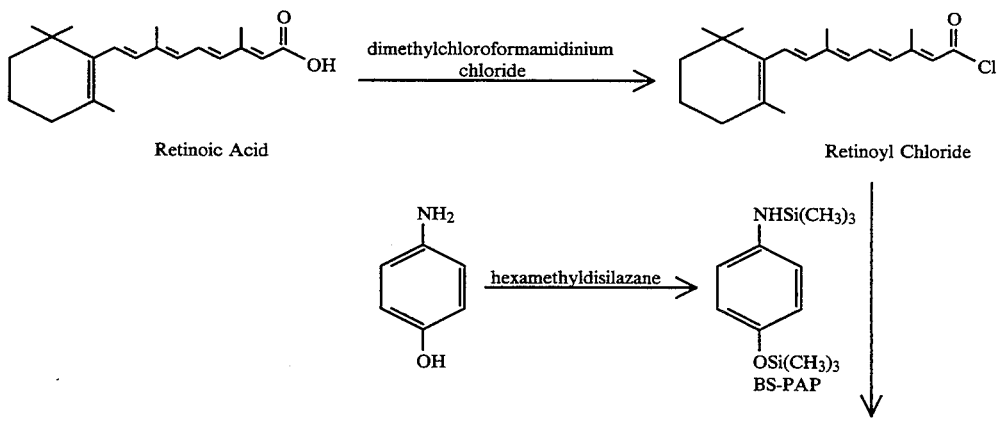

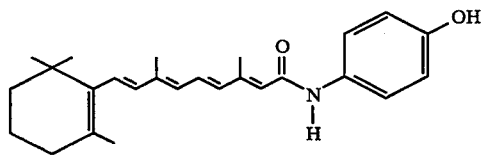

4-Hydroxyphenylretinamide

In accordance with the process of the invention, a slurry of retinoic acid in N,N-dimethylformamide (DMF) is reacted with dimethylchloroformamidinium chloride at ambient temperature to yield retinoyl chloride. The solution of retinoyl chloride is added to a DMF solution of the novel intermediate bis-(N,O)-trimethylsilyl-p-aminophenol (BS-PAP) at low temperature (5°–12° C.). The novel intermediate BS-PAP is produced by reacting p-aminophenol with hexamethyldisilazane. An instantaneous reaction on the nitrogen of the BS-PAP occurs: the trimethylsilyl group on nitrogen is activated by electrophilic addition (acylation) and the trimethylsilyl group on the oxygen protects the phenol from oxygen acylation. The silicon by-product of nitrogen acylation is trimethylsilylchloride which is believed to be converted to polymeric siloxanes during workup and the final product is separated from the by-product by filtration.

Subsequently adding a solution of potassium fluoride to the reaction mixture leads to crystallization of product from the reaction mixture as a DMF·4-HPR solvate. This product is then recrystallized from ethanol/water to provide high purity (>99%) 4-HPR in a final yield of 85–90% from retinoic acid. Large scale examples of each step of the process are provided in the Examples section.

This invention describes mild and rapid conditions which produce retinoyl chloride in high yield and purity. The retinoyl chloride is not isolated but is used in situ in the next step of the process; thus eliminating an opportunity for degradation. The retinoyl chloride is reacted with an activated form of p-aminophenol (i.e. BS-PAP); use of the activated amine allows amide formation under mild conditions (e.g. under 20° C.) and also provides protection to the reactive phenolic oxygen. The overall yield of the conversion of retinoic acid to 4-HPR under the conditions described in the invention, is generally over 80% and typically 85–90% of 4-HPR with a purity of >99%. When all-trans-retinoic acid is used analogous yields of all-trans-4-HPR are observed. This is a marked improvement over the currently available processes.

In other preferred embodiments of the invention the 4-HPR is eventually formed and isolated by the additional steps of: adding an aqueous solution of potassium fluoride to the reaction mixture of dimethylformamide and 4-HPR to form a crystalline solvate thereof; and subsequently recrystallizing the solvate in an ethanol/water or toluene/acetone solution to provide substantially pure 4-HPR. Preferably, the ratio of ethanol/water is from about 2 to 10:1 at a concentration of 4-HPR of from about 10 to 20% weight by total weight of the solution. In preferred embodiments the crystallization temperature is from about 0° to 80° C.

The above recrystallization is designed to produce the "A" form polymorph of 4-HPR which has been found to be more stable than any other known polymorphic forms of 4-HPR.

The invention will now be illustrated by Examples. The Examples are not intended to be limiting of the scope of the present invention but read in conjunction with the detailed and general description above, provide further understanding of the invention and outline a process for preparing the intended product of the process of the invention as well as producing the intermediate compounds of the invention.

EXAMPLES

The following ingredients, processes and procedures for practicing the process of the present invention correspond to that described above. The procedures below describe with particularity a presently preferred embodiment of the process of the invention for large scale production of all-trans-4-HPR. Any methods, starting materials, reagents or excipients which are not particularly described will be generally known and available to those skilled in the pharmaceutical and chemical process arts.

Example 1

Preparation of Bis-(N,O)-Trimethylsilyl-P-Aminophenol (BS-PAP)

In a 3-neck flask equipped with an overhead stirrer, condenser with bubbler, thermometer and heating mantle, p-aminophenol (98% 2180.0 g, , 20.0 m) and hexamethyldisilazane (technical grade, 99.0% min., 4335.5 g, 26.9 m) were heated together slowly with stirring. Ammonia gas evolved gradually until the temperature reached ca. 85° C., whereupon evolution became rapid. After the vigorous evolution of ammonia subsided, the temperature was increased gradually to 150°–160° C. for 3.5 hours. When the reaction was complete, the excess reagent was removed by distillation at 10 torr. The product was purified by distillation at 120° C. at 0.5 torr; yield 4850.0 g (96%). The purified material was a yellow oil which eventually crystallized on standing (mp 60°–63° C.). The compound should be stored and transferred under argon as it is moisture sensitive.

Example 2

Preparation of Dimethylchloroformamidinium Chloride

This intermediate was prepared according to the method of H. H. Bosshard, et al., *Helv. Chim. Acta.*, 42, 1959, 1653. Dry DMF (224 g, 3.06 m) in diethyl ether (6.6 L) in a 12 L, 3-neck round bottom flask was treated with oxalyl chloride (390 g, 3.07 m) as rapidly as the evolution of gases allowed; a colorless precipitate was immediately evident and the reaction was endothermic. After 1 hour, the solvent was evaporated under vacuum. When removing the flask from the vacuum, argon was bled into the system.

Example 3

Preparation of All-Trans-Retinoyl Chloride

A slurry of retinoic acid (all-trans, 860 g, 2.86 m) in DMF (3.5 L) was added to the crude white solid dimethylchloroformamidinium chloride (from Example 1). After stirring at room temperature for 45 minutes, the clear deep red retinoyl chloride solution was cooled in ice. This solution is then used in the synthesis of carboxylate derivatives such as 4-HPR.

Example 4

Preparation of All-Trans-N-(4-Hydroxyphenyl)-Retinamide

A solution of BS-PAP (4850.0 g, 19.0 m) in DMF (1.0 L) was cooled in an ice-salt bath to 0° C. A freshly prepared solution of retinoyl chloride [prepared as in Example 3 1824.0 g, 5.72 m retinoyl chloride] was cooled to ca. 10° C. (protected from light). The acid chloride solution was gradually added over about 1.5 hours to the BS-PAP solution while maintaining the temperature between 10°-15° C. (the reaction is exothermic). The reaction temperature should not exceed 20° C. to avoid product degradation and diminution of product purity. Upon completion of the addition, stirring was continued for ca. 1.5 hours at ambient temperature. The reaction mixture was then stirred rapidly while a solution of potassium fluoride dihydrate (600.0 g, 6.37 m) in water (4-5 L) was added at such a rate that the temperature did not exceed 15° C. and stirring was continued until crystallization was complete. The crude product was collected by filtration, washed with water, and vacuum dried. The product is then recrystallized from ethanol/water as described below and dried to routinely yield 84-90% of all-trans-4-HPR of >99% purity.

Example 5

Recrystallization of N-(4-Hydroxyphenyl)-Retinamide

Water-wet N-(4-hydroxyphenyl)-retinamide (4-HPR) from Example 4 was dissolved by adding it gradually to boiling 95% ethanol (8.0 L). The warm solution was then filtered. The filtrate was reheated to boiling and water (2.4 L) was added. The solution was then allowed to stand without agitation until crystallization began. At that point the vessel was placed in an ice-water bath and stirred occasionally to maintain a slurry. Cooling was applied for 4 hrs. The purified product was collected by filtration and washed with ethanol/water (60/40-v/v) until the filtrate was only slightly colored (pale yellow), (about 2-3 liters of wash solvent). The product was then dried in vacuo (10 mm), without heating, for 48 hrs. The resulting intensely yellow solid should be protected on storage from exposure to light, air, heat, and moisture by sealing it under argon in refrigerated containers. Product purity is determined by hplc analysis (>99.0% typical for purified 4-HPR). By means of x-ray analysis, the solid was determined to be exclusively the "A-form" of the polymorphic crystal. The yield of recrystallization was 92.9%.

The scope of the present invention is not limited by description, examples and suggested methods described herein and modifications can be made without departing from the spirit of the invention. For example, other halides may be substituted for the chloride in retinoyl chloride, e.g. retinoyl bromide, by substituting the desired halide in the dimethylformamidinium reagent.

Further, other carboxylate derivatives of retinoyls may be prepared in accordance with various modifications of the general process of the invention as would be known by those skilled in the art.

Applications of the compositions, processes, and method of the present invention can be accomplished by any chemical and pharmaceutical methods and techniques as are presently or prospectively known to those skilled in the art. It is intended that the invention cover any modifications and variations of this invention provided that they come within the scope of the appended claims and their equivalents.

What is claimed is:

1. A mild, high yield process for the large scale synthesis of N-(4-hydroxyphenyl)-retinamide comprising the steps of:
   reacting retinoic acid with dimethylchloroformamidinium chloride at ambient temperature to form retinoyl chloride; and
   reacting retinoyl chloride with a tertiary substituted, bis-(N,O)-(silyl)-p-aminophenol of the formula bis-($R_1$,$R_2$, $R_3$silyl)-p-aminophenol wherein $R_{1-3}$ are the same or different and are phenyl or $C_{1-5}$ alkyl, at a temperature of below 20° C. to eventually form N-(4-hydroxyphenyl)-retinamide.

2. The process of claim 1 wherein the retinoic acid, retinoyl chloride and N-(4-hydroxyphenyl)-retinamide are the substantially pure trans-stereoisomer thereof.

3. The process of claim 1 wherein the yield of N-(4-hydroxyphenyl)-retinamide is at least 80% from retinoic acid.

4. The process of claim 1 wherein the retinoyl chloride is formed and reacted in situ with bis-($R_1$,$R_2$,$R_3$ silyl)-p-aminophenol to eventually form N-(4-hydroxyphenyl)-retinamide.

5. The process of claim 1 wherein the bis-(silyl)-p-aminophenol is bis-(N,O)-trimethylsilyl-p-aminophenol.

6. The process of claim 1 wherein the retinoic acid is reacted in a polar or dipolar aprotic solvent.

7. The process of claim 1 wherein retinoic acid is reacted in a solvent selected from the group consisting of N,N-dimethylformamide; N,N-dimethylacetamide; and N-methylpyrrolidinone.

8. The process of claim 1 wherein retinoyl chloride is reacted with bis-(N,O)-trimethylsilyl-p-aminophenol in an aprotic polar or dipolar solvent.

9. The process of claim 1 wherein retinoyl chloride is reacted with bis-(N,O)-trimethylsilyl-p-aminophenol in a solvent selected from the group consisting of N,N-dimethylformamide; N,N-dimethylacetamide; and N-methylpyrrolidinone.

10. The process of claim 4 wherein retinoyl chloride is formed and reacted with bis-(N,O)-trimethylsilyl-p-aminophenol in dimethylformamide.

11. The process of claim 1 wherein the bis-(N,O)-trimethylsilyl-p-aminophenol is prepared by reacting p-aminophenol and hexamethyldisilazane.

12. The process of claim 1 wherein the N-(4-hydroxyphenyl)-retinamide is isolated by the additional steps of: adding an aqueous solution of potassium fluoride to the reaction mixture of dimethylformamide and N-(4-hydroxyphenyl)-retinamide to form a crystalline solvate thereof; and subsequently recrystallizing the solvate in an ethanol/water solution to provide substantially pure N-(4-hydroxyphenyl)-retinamide.

13. The process of claim 12 wherein the N-(4-hydroxyphenyl)-retinamide is recrystallized in an ethanol/water solution with a ratio of from about 2 to 10:1, ethanol: water, at a concentration of from about 10 to 20% of N-(4-hydroxyphenyl)-retinamide weight by total weight of the solution, and at a crystallization temperature of about 0° to 80° C.

14. The process of claim 5 wherein the N-(4-hydroxyphenyl)-retinamide is isolated by the additional steps of: adding an aqueous solution of potassium fluoride to the reaction mixture of dimethylformamide and N-(4-hydroxyphenyl)-retinamide to form a crystalline solvate thereof; and subsequently recrystallizing the solvate in an ethanol/water solution to provide substantially pure N-(4-hydroxyphenyl)-retinamide.

15. The process of claim 14 wherein the N-(4-hydroxyphenyl)-retinamide is recrystallized in an ethanol/water solution with a ratio of from about 2 to 10:1, ethanol: water, at a concentration of from about 10 to 20% of N-(4-hydroxyphenyl)-retinamide weight by total weight of the solution, and at a crystallization temperature of about 0° to 80° C.

16. The process of claim 1 wherein the retinoyl chloride is formed in the absence of a decomposition-catalyzing base.

17. A method of using bis-($R_1,R_2,R_3$silyl)-p-aminophenol as an intermediate to eventually produce N-(4-hydroxyphenyl)-retinamide wherein $R_{1-3}$ are the same or different and are phenyl or $C_{1-5}$ alkyl.

18. The method of claim 17 wherein the bis-(silyl)-p-aminophenol is bis-(N,O)-trimethylsilyl-p-aminophenol.

19. A method of using bis-($R_1,R_2,R_3$silyl)-p-aminophenol as an intermediate to eventually produce a hydroxyphenylamide.

20. The method of claim 19 wherein the bis-(silyl)-p-aminophenol is bis-(N,O)-trimethylsilyl-p-aminophenol.

* * * * *